United States Patent
Simons

(10) Patent No.: US 9,061,926 B2
(45) Date of Patent: Jun. 23, 2015

(54) SYNERGISTIC COMPOSITION AND METHOD FOR INHIBITING GROWTH OF MICROORGANISMS

(75) Inventor: Bert Simons, Amstelveen (NL)

(73) Assignee: NALCO COMPANY, Naperville, IL (US)

( * ) Notice: Subject to any disclaimer, the term of this patent is extended or adjusted under 35 U.S.C. 154(b) by 1745 days.

(21) Appl. No.: 11/183,060

(22) Filed: Jul. 15, 2005

(65) Prior Publication Data

US 2007/0012632 A1     Jan. 18, 2007

(51) Int. Cl.
| | |
|---|---|
| *A01N 43/00* | (2006.01) |
| *A61K 31/33* | (2006.01) |
| *C02F 1/50* | (2006.01) |
| *A01N 43/50* | (2006.01) |
| *A01N 59/00* | (2006.01) |

(52) U.S. Cl.
CPC . *C02F 1/50* (2013.01); *A01N 43/50* (2013.01); *A01N 59/00* (2013.01)

(58) Field of Classification Search
None
See application file for complete search history.

(56) References Cited

U.S. PATENT DOCUMENTS

| | | | | |
|---|---|---|---|---|
| 5,494,588 | A * | 2/1996 | LaZonby | 210/755 |
| 5,565,109 | A * | 10/1996 | Sweeny | 210/755 |
| 5,736,057 | A * | 4/1998 | Minotti | 210/759 |
| 6,429,181 | B2 | 8/2002 | Sweeny et al. | |
| 6,447,722 | B1 * | 9/2002 | Rakestraw | 422/37 |
| 2003/0029812 | A1 | 2/2003 | Burns et al. | |
| 2003/0211210 | A1 * | 11/2003 | Howarth | 426/332 |

FOREIGN PATENT DOCUMENTS

| | | | |
|---|---|---|---|
| WO | WO 2004060818 | | 7/2004 |
| WO | WO 2004060818 | A1 * | 7/2004 |

OTHER PUBLICATIONS

Knapick et al "A brominated methylethylhydantoin slimicide in a tissue mill", TAPPI Journal May 2003.*

* cited by examiner

*Primary Examiner* — Jennifer M Kim
*Assistant Examiner* — Jean Cornet
(74) *Attorney, Agent, or Firm* — Benjamin Carlsen

(57) ABSTRACT

The present invention provides a composition and method for inhibiting the growth of microorganisms in industrial water systems. Methods employing the composition comprising halogen-based hydantoin or hydantoin-stabilized halogen in combination with peracetic acid demonstrate synergistic control of microbial growth, particularly control of slime deposition.

18 Claims, No Drawings

SYNERGISTIC COMPOSITION AND METHOD FOR INHIBITING GROWTH OF MICROORGANISMS

FIELD OF THE INVENTION

The present invention relates generally to controlling the growth of microorganisms in industrial waters. More specifically, the present invention relates to the use of a composition for inhibiting microbial growth, especially inhibition of slime deposits, comprising peracetic acid and a composition comprising hydantoin-stabilized halide or halogen-based hydantoin.

BACKGROUND OF THE INVENTION

The presence of microorganisms in water systems, especially industrial water systems, have resulted in extensive research efforts to identify biocidal compositions for industrial manufacturers where microbial growth is an extensive and constant problem. Examples of industrial waters where microorganisms can interfere with industrial processes include: cooling tower waters, mining process waters, food processing waters, papermaking slurries, pulp and paper mill waters, sugar reprocessing waters, and the like. To counteract the detrimental effects of microbial growth, manufacturers must employ expensive microbial control programs. These effects impact the efficacy of industrial processes by causing, for example, plugging of pumps and membranes, corrosion under the deposits, and odors.

The formation of slimes by microorganisms is an additional problem that is encountered in many aqueous systems. Slime deposition is found in natural and industrial waters that possess conditions that are conducive to the growth and reproduction of slime-forming microorganisms. For example, in the paper industry, microorganisms can adversely affect finished paper products. Contaminating microorganisms are a major cause of spoilage of pulp, furnish, coatings, or additives.

The problems identified above have resulted in the extensive utilization of biocides in aqueous systems, such as pulp and paper mill systems. To date, no one compound or composition has achieved a clearly established predominance in respect to the problems discussed above. For these reasons, control of microorganisms and slime in industrial waters remain an unfelt need.

SUMMARY OF THE INVENTION

Compositions and methods are provided which provide unexpected synergistic inhibition of growth of microorganisms, inhibition of slime deposits, without the use of high, and/or damaging levels of biocides.

The compositions include:
(1) a first composition comprising (a) hydantoin-stabilized alkali or alkaline earth metal halide ion donor; or (b) halogen-based hydantoin; and
(b) a second composition comprising peracetic acid (PAA), characterized in that the dosing of each composition in process waters results in a synergy for controlling microbial growth.

Halide ion donors may be any oxidizing halogen such as chlorine or bromine. An efficacious form of chlorine is hypochlorite. Alkali or alkaline earth metal hypochlorite is selected from the group consisting of sodium hypochlorite, potassium hypochlorite, lithium hypochlorite, magnesium hypochlorite, calcium hypochlorite, and mixtures thereof.

Halogen-based hydantoin includes bromo- or chloro-hydantoin

A representative composition comprises a first composition of hydantoin-stabilized sodium hypochlorite and a second composition of peracetic acid (PAA).

Although hydantoin, hypochlorite, and peracetic acid are known biocidal compounds, the synergistic effect obtained by combining PAA and a hydantoin-stabilized hypochlorite has not been previously reported.

DETAILED DESCRIPTION OF THE INVENTION

Definitions

As used herein, the following terms are defined as:

"About" means within 50%, preferably within 25%, and more preferably within 10% of a given value or range. Alternatively, the term "about" means within an acceptable standard error of the mean, when considered by one of ordinary skill in the art.

"Effective amount": means any dosage of biocidal composition that controls the growth of bacterial microbes in industrial water systems.

"Halide ion donors" are forms hydantoin or of chloride or bromide used as oxidizing biocides or hydantoins substituted with at least one halogen.

"Slime" means an accumulation of certain microorganisms in the presence of pulp fiber, filler, dirt and other materials, mixed in varied proportions, having variable physical characteristics and accumulating at continuously changing rates. In most industrial process waters, especially pulp and paper mill systems, spore forming bacteria and *Pseudomonas aeruginosa* contribute to slime formation.

"First Composition" comprises halogen-based hydantoin or hydantoin-stabilized alkali or alkaline earth metal halide ion donor; including but not limited to sodium hypochlorite.

"Second Composition" comprises peracetic acid (PAA),

"Synergistic Composition" is greater than expected control of microorganisms in process waters comprising the combination of the above-identified first and second compositions.

Compositions comprising peracetic acid ("PAA") and hydantoin-stabilized hypochlorite or halogen-based hydantoin are especially efficacious in controlling the growth of bacterial microbes in industrial water systems. Specifically, mixtures of PAA and hydantoin-stabilized hypochlorite are especially efficacious in controlling the growth of bacterial microbes, and especially the build-up of slime deposits.

The first active component of the synergistic composition is alkali or alkaline earth metal halide donor or halogen-derived hydantoin. For ease of discussion, hypochlorite will be exemplified. The hypochlorite, includes but is not limited to, sodium hypochlorite, potassium hypochlorite, lithium hypochlorite, magnesium hypochlorite or calcium hypochlorite. Bromo-based hydantoin is another useful exemplification.

Sodium hypochlorite in pure form is unstable. Industrial bleach consists of a solution of sodium hypochlorite ranging from 10% to 13% available chlorine by volume (8.8%-10.6% by weight). One gallon of bleach contains about the same amount of active chlorine as one pound of chlorine gas.

The second active component of the synergistic composition is hydantoin. Hydantoin is represented by

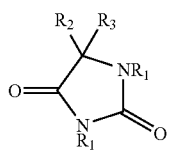

wherein:
Each $R_1$ can be the same or different and independently represent H or $OR_4$, $R_4$ is H, halogen, or alkyl of 1 to 5 carbon atoms, and $R_2$ and $R_3$ are the same or different or independently H or alkyl of 1 to 5 carbon atoms. When hydantoin is the halogen source, the stabilization of the oxidizing biocide hypochlorite is optional. Dialkyl-substituted hydantoin compounds exemplify additional stabilizers. For example, 5,5-dimethylhydantoin (DMH) or methylethylhydantoin (MEH) provide effective hypochlorite stabilization for synergistic microbial control with PAA.

The third active component is PAA. Peracetic acid is a unique oxidant, utilizing a different mode of action than other oxidants. Given the structure of the molecule

the hydrocarbon tail allows PAA to penetrate into the bacterial cell. This enables the molecule to disrupt S—S and S—H bonds both inside and outside of the organisms, killing more quickly and effectively than other oxidants. Other oxidants, such as $HOCl$, $ClO_{·2}$, $H_2O_{·2}$, etc. do not penetrate the cells in this manner because they do not have an organic portion to facilitate entrance into the bacterial cell. Peracetic acid has always been applied by itself in high concentrations but has never been used for effective microbial control at concentration levels identified herein. The synergistic activity supplied by the active components of the first composition permit lower PAA concentrations for effective control. Peracetic acid has been used as a sterilant in the food industry for many years, but is generally used at higher concentrations (10,000 to 100,000 ppm). The combined treatment is added, for example, to cooling water systems, paper and pulp mill systems, pools, ponds, lagoons, lakes, etc., to control the formation of bacterial microorganisms, which may be contained by, or which may become entrained in, the system to be treated.

It has been found that the PAA and hydantoin-stabilized hypochlorite compositions and methods of utilization of the treatment are efficacious in controlling against filamentous bacteria. Filamentous bacteria play a major role in the formation of many slime deposits. Additionally, dimethylhydantoin-stabilized hypochlorite has been reported as very effective in slime control (which may populate these systems. The combined treatment composition and method is expected to be efficacious in inhibiting and controlling all types of aerobic and anaerobic bacteria.

Increased inhibition of microbial growth resulting from compositions having hydantoin-stabilized hypochlorite as an active ingredient are mixed with compositions having PAA as an active ingredient provide a higher degree of bactericidal activity than that of the individual ingredients comprising the mixture. Accordingly, it is possible to produce a highly efficacious bactericide. Because of the enhanced activity of the mixture, the total quantity of the bacterial treatment may be reduced. The combined PAA and hydantoin-stabilized hypochlorite biocide treatment may be added to the desired aqueous system in need of biocidal treatment The combination of PAA and hydantoin-stabilized possess a higher degree of bactericidal activity than that of the individual ingredients comprising the mixture.

In the present invention the hydantoin-stabilized hypochlorite is generated on site by mixing a hydantoin solution, for example a solution containing dimethylhydantoin, with a sodium hypochlorite solution. These two components can be mixed in different ratios depending on the chlorine demand of the system, and then be dosed in the process water. It is also possible to dose the hydantoin and hypochlorite compositions separately in the water that needs to be treated, in a side stream of the process water that need to be treated, or other carrier water (e.g. freshwater), that supplies the process water with sufficient amounts of hydantoin-stabilized hypochlorous acid. The second oxidizing biocide peracetic acid is dosed in the process water containing the stabilized chlorine. Preferably the amount of free halogen coming from the hydantoin-stabilized solution should be low, at the point were the second oxidant is applied. This will prevent antagonism between hypochlorite and the second oxidant. The efficiency in microbial control can be further enhanced by the addition of conventional biocides.

The advantage of using a combination of hydantoin-stabilized hypochlorite and PAA as a second oxidant is that it lowers the overall use of oxidizing biocides in the process that is needed for inhibition of the growth of microorganisms. As hydantoin-stabilized hypochlorite has been shown to work excellent in control of slime deposition, whereas peracetic acid can be very effective reducing numbers of microorganisms, a complementary effect in control of microorganisms in industrial waters can be expected. This is especially the case when control of slime deposition is desirable.

The use of other biocidal components, preferably so-called fast killers, including but not limited to, dibromonitrile propionamide (DBNPA), will complement the dimethylhydantoin-stabilized hypochlorite in killing efficiency, thus greatly expanding the possible applications in industries. The synergy that was found between dimethylhydantoin-stabilized hypochlorite and PAA, allows reduced use of these chemicals thus ameliorating the problems caused by excess of hypochlorite. Furthermore, PAA was shown to contribute far less to corrosion, or felt damage, and does not interfere with wet-end chemicals in papermaking, for example optical brightening agents, dyes, sizing agents and the like. On top of this PAA does not contribute to the formation of AOX. Final breakdown products of PAA are carbon dioxide and water, thus no harmful products will reach the environment. Thus PAA is a preferred option in case health concerns associated with non-oxidizing biocides are a concern, or the mill wishes to promote a green image. On the negative side PAA alone is less effective in slime control compared to dimethylhydantoin-stabilized hypochlorite.

All of the reasons mentioned above make it extremely desirable to be recognized as the inventor of control of microorganisms in industrial waters by applying combinations of dimethylhydantoin stabilized hypochlorite, and PAA in such waters.

Applications including PAA are very common in paper industry. A weakness of this technology is poor control in the so called long loops, comprising the white water that is not directly used to dilute the pulp just prior to the paper formation section (in the so-called short loop), but that is reused for example in re-pulping of pulp and broke, and/or showers after clearing. Thus, the composition as identified fulfills an unmet need in the industry.

The following experimental data were developed. It is to be remembered that the following examples are to be regarded solely as being illustrative, and not as restricting the scope of the invention.

Hydantoin-stabilized hypochlorite combined with PAA were tested in accordance with the procedure described below. In determining synergy: Q.sub.a=quantity of compound A, acting alone, producing an end point
Q.sub.b=quantity of compound B, acting alone, producing an end point
$Q_A$=quantity of compound A in mixture, producing an end point
$Q_B$=quantity of compound B in mixture, producing an end point
The end point used in the calculations is the % reduction caused by each mixture of A and B. $Q_A$ and $Q_B$ are the individual concentrations in the A/B mixture causing a given % reduction. $Q_a$ and $Q_b$ are determined by interpolation from the respective dose response curves of A and B as those concentrations of A and B acting alone which produce the same % reduction as each specific mixture produced.

The data in the following tables come from treating microorganisms found in industrial cooling waters and in pulping and paper making systems, with varying ratios and concentrations of PAA and DMH-hypochlorite. Shown for each combination is the % reduction of bacterial activity, the calculated SI, and the weight ratio of PAA and DMH-hypochlorite.
The following experimental data were developed. It is to be remembered that the following examples are to be regarded solely as being illustrative, and not as restricting the scope of the invention.

Example 1

Mill Producing Paper Grades Using Mechanical Pulp in the Furnish

The furnish used in this mill is composed of about 50% TMP, 25% bleached Kraft pulp, and 25% broke. White water was collected and total bacterial counts were determined in samples with and without the addition of DMH stabilized chlorine (1:1 molar ratio of DMH to "Cl2) and/or PAA, after 50 minutes of contact time. The results are summarized in the table below.

| Biocide (PAA: ppm product; DMH stabilized chlorine: ppm Cl2) | Total bacterial counts |
| --- | --- |
| Control (no biocide added) | $1.3 \times 10^7$ |
| PAA-25 | $4 \times 10^6$ |
| PAA-50 | $3 \times 10^5$ |
| PAA-100 | $3 \times 10^3$ |
| Cl2-1 | $10^7$ |
| Cl2-2 | $4 \times 10^6$ |
| Cl2-4 | $<10^3$ |
| Cl2-2 + PAA-25 | $10^4$ |
| Cl2-2 + PAA-50 | $<10^3$ |

This example shows the synergistic relationship obtained with the present invention. Synergy is mathematically demonstrated by the industry accepted method described by Kull et al. (Applied Microbiology (1961), Vol. 9: 538-541. Applied to the current invention it is as follows:
 $Q_A$=ppm of active peracetic acid alone, which produces an endpoint
 $Q_B$=ppm of active DMH stabilized chlorine (expressed as ppm Cl2) alone, which produces an endpoint;
 $Q_a$=ppm of active peracetic acid, in combination, which produces an endpoint
 $Q_b$=the ppm of active DMH stabilized chlorine (expressed as ppm Cl2), in combination, which produces an endpoint
$Q_a/Q_A + Q_b/Q_B$=synergy index
If Synergy index (SI) is:
 <1, it indicates synergy
 1, it indicates additivity
 >1, it indicates antagonism
According to this example, a>3-log reduction in bacterial counts is achieved with:
Synergistic Composition:
Composition 1: PAA=100 ppm
Composition 2: DMH stabilized chlorine ("Cl2")=4 ppm
PAA=25 ppm+"Cl2"=2 ppm
$Q_a/Q_A + Q_b/Q_B = 25/100 + 2/4 = 0.75$ Example 2

Mill Producing Paper Grades Using Chemical Pulp

The furnish used on this paper machine is composed of about 60% bleached Kraft pulp, and 40% broke. White water was collected and total bacterial counts were determined in samples with and without the addition of DMH stabilized chlorine (1:1 molar ratio of DMH to "Cl2"), and/or PAA, after 30 minutes of contact time. The results are summarized in the table below.

| Biocide (PAA: ppm product; DMH stabilized chlorine: ppm Cl2) | Total bacterial counts |
| --- | --- |
| Control (no biocide added) | $5.8 \times 10^6$ |
| PAA-2.5 | $5.8 \times 10^6$ |
| PAA-5 | $1.1 \times 10^6$ |
| PAA-10 | $5 \times 10^4$ |
| Cl2-2.5 | $2.7 \times 10^4$ |
| Cl2-5 | $6 \times 10^2$ |
| Cl2-2.5 + PAA-2.5 | $2 \times 10^3$ |

In this example a>3-log reduction in bacterial counts is achieved with:
 Synergistic Composition:
 Composition 1: PAA>10 ppm
 Composition 2: DMH stabilized chlorine ("Cl2")=5 ppm
 PAA=2.5 ppm+"Cl2"=2.5 ppm
 $Q_a/Q_A + Q_b/Q_B = 2.5/>10 + 2.5/5 = <0.75$ Example 3

Very Closed Mill (<5 m³/Ton) Producing Paper Grades Using Chemical Pulp

The furnish used in this mill is composed of about 75% bleached Kraft pulp, and 25% broke. White water was collected and total bacterial counts were determined in samples with and without the addition of DMH stabilized chlorine (1:1 molar ratio of DMH to "Cl2"), and/or PAA, after 30 minutes of contact time. The results are summarized in the table below.

| Biocide (PAA: ppm product; DMH stabilized chlorine: ppm Cl2) | Total bacterial counts |
| --- | --- |
| Control (no biocide added) | $9 \times 10^6$ |
| PAA-50 | $4.5 \times 10^6$ |
| PAA-75 | $1.6 \times 10^6$ |
| PAA-100 | $3 \times 10^5$ |

| Biocide (PAA: ppm product; DMH stabilized chlorine: ppm Cl2) | Total bacterial counts |
|---|---|
| PAA-150 | $10^3$ |
| PAA-200 | $<10^2$ |
| Cl2-1 | $9 \times 10^6$ |
| Cl2-2 | $9 \times 10^6$ |
| Cl2-3 | $6.3 \times 10^6$ |
| Cl2-4 | $5.4 \times 10^6$ |
| Cl2-1 + PAA-100 | $9 \times 10^4$ |
| Cl2-1 + PAA-150 | $<10^2$ |

In this example a 2-log reduction in bacterial counts is achieved with:
Synergistic Composition
Composition 1: PAA 150 ppm
Composition 2: DMH stabilized chlorine ("Cl2")=>4 ppm
PAA=100 ppm+"Cl2"=1 ppm
$Q_a/Q_A+Q_b/Q_B=100/150+1/>4=0.67+<0.25=<0.92$

What is claimed is:

1. A composition for inhibiting the growth of microorganisms comprising effective amounts of:
a first oxidizing composition comprising hydantoin stabilized hypochlorite,
long loop white water from a paper pulping process, and
a second oxidizing composition comprising peracetic acid or salts thereof;
wherein the hydantoin stabilized hypochlorite comprises a hypochlorite portion and a hydantoin portion, the hypochlorite portion of the hydantoin stabilized hypochlorite comprises an alkali- or alkaline salt of hypochlorite, the hydantoin portion of the hydantoin stabilized hypochlorite comprises a hydantoin-based halide or hydantoin represented by formula (1):

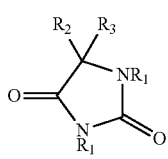

Formula (1)

wherein:
$R_1$ is the same or different; when different it independently represents H or $OR_4$, wherein $R_4$ is H, halogen, or alkyl of 1 to 5 carbon atoms, and
$R_2$ and $R_3$ are the same or different; when different they independently represent H or alkyl of 1 to 5 carbon atoms;
and
peracetic acid and the hydantoin stabilized hypochlorite are at a total concentration of about 25 ppm or less;
peracetic acid and the hydantoin stabilized hypochlorite are in a molar ratio of at least about 1 to 1; and
the composition displays a synergy index of less than 1.

2. The composition of claim 1, further comprising a halogen based hydantoin.

3. The composition of claim 1, further comprising a hydantoin chloride.

4. The composition of claim 1, wherein $R_1$ of formula (1) are each H, $R_2$ and $R_3$ are different and independently $C_1$ to $C_5$ alkyl and the hypochlorite portion is sodium hypochlorite.

5. The composition of claim 1, in which the hydantoin portion is a dialkyl hydantoin.

6. The composition of claim 1, in which the composition displays a synergy index of less than 0.98.

7. The composition of claim 1, used to control slime deposition in industrial water systems.

8. The composition of claim 1, used to control growth of filamentous bacteria in industrial water systems.

9. The composition of claim 1, used to control slime deposition in a papermaking process.

10. The composition of claim 1, further comprising a fast acting biocide.

11. The composition of claim 1, wherein the composition displays at least a 2-log reduction in bacterial count within 50 minutes of formation of the composition.

12. The composition of claim 1, wherein the composition displays at least a 3-log reduction in bacterial count within 50 minutes of formation of the composition.

13. The composition of claim 1, wherein the composition displays at least a 3-log reduction in bacterial count within 30 minutes of formation of the composition.

14. The composition of claim 1, wherein the composition displays at least a 4-log reduction in bacterial count within 30 minutes of formation of the composition.

15. The composition of claim 1, wherein the hydantoin stabilized hypochlorite is at a concentration of about 2.5 ppm or less.

16. The composition of claim 1, wherein peracetic acid and the hydantoin stabilized hypochlorite are in a molar ratio of at least about 12 to about 1.

17. The composition of claim 1, used to control bacterial growth in a mechanical pulping process.

18. The composition of claim 1, used to control bacterial growth in a chemical pulping process.

* * * * *